(12) United States Patent
Moschwitzer (10) Patent No.: US 8,034,381 B2
(45) Date of Patent: *Oct. 11, 2011

(54) METHOD FOR PRODUCING ULTRAFINE SUBMICRONIC SUSPENSIONS

(75) Inventor: Jan Moschwitzer, Berlin (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 754 days.

This patent is subject to a terminal disclaimer.

(21) Appl. No.: 11/908,153

(22) PCT Filed: Mar. 9, 2006

(86) PCT No.: PCT/EP2006/002176

§ 371 (c)(1),
(2), (4) Date: May 23, 2008

(87) PCT Pub. No.: WO2006/094808

PCT Pub. Date: Sep. 14, 2006

(65) Prior Publication Data

US 2008/0279928 A1    Nov. 13, 2008

(30) Foreign Application Priority Data

Mar. 11, 2005  (DE) .......................... 10 2005 011 786

(51) Int. Cl.
*A61K 9/14* (2006.01)

(52) U.S. Cl. ...................................................... 424/489
(58) Field of Classification Search .................. None
See application file for complete search history.

(56) References Cited

U.S. PATENT DOCUMENTS

| | | | |
|---|---|---|---|
| 5,389,382 A | 2/1995 | List | |
| 5,858,410 A | 1/1999 | Muller | |
| 6,018,080 A | 1/2000 | Dearn | |
| 6,251,945 B1 | 6/2001 | Einig | |
| 6,551,619 B1 * | 4/2003 | Penkler et al. | 424/489 |
| 6,565,885 B1 | 5/2003 | Tarara | |
| 6,607,784 B2 | 8/2003 | Kipp | |
| 6,696,084 B2 | 2/2004 | Pace | |
| 2002/0056206 A1 | 5/2002 | Pace | |
| 2003/0175313 A1* | 9/2003 | Garrec et al. | 424/400 |
| 2003/0229015 A1 | 12/2003 | Fogelman | |

FOREIGN PATENT DOCUMENTS

| | | |
|---|---|---|
| CA | 2375992 A1 * | 1/2001 |
| DE | 4440337 A1 | 5/1996 |
| WO | 9632095 A1 | 10/1996 |
| WO | 0103670 A1 | 1/2001 |
| WO | 0145677 A1 | 6/2001 |
| WO | 2004060244 A1 | 7/2004 |
| WO | 2004060344 A1 | 7/2004 |

OTHER PUBLICATIONS

Rios, "Brining Formulations to Size, Strategies for Micro- and Nanoparticle Development," Pharmaceutical Technology, Nov. 2004, www.pharmtech.com.
Uekama K. Design and Evaluation of Cyclodextrin-Based Drug Formulation. Chem Pharm Bull, vol. 52, 900-915 (2004) 2004;52(8):900-15.
Merisko-Liversidge E. Nanocrystals: Resolving Pharmaceutical Formulation Issues associated with poorly water-soluble Compounds. In: Marty JJ, editor. Particles; 2002; Orlando: Marcel Dekker; 2002.
Buchmann S, Fischli, W., Thiel, F. P., Alex, R. Aqueous microsuspension, an alternative intravenous formulation for animal studies. In: 42 nd Annual Congress of the International Association for Pharmaceutical Technology (APV); 1996; Mainz; 1996. p. 124.
Mosharraf, M., Nyström, C., The effect of particle size and shape on the surface specific dissolution rate of micronised practically insoluble drugs.Int. J. Pharm., 122, 35-47, 1995.
Rainer H. Muller, Jan Moschwitzer and Faris Nadiem Bushrab, Manufacturing of nanoparticles by milling and homogenization techniques, eds. Gupta, Kompella, Publisher: Marcel Dekker, summitted for printing Jan. 2006; "Nanopartcle Technology for Drug Delivery" Chapter 2 pp. 21-51.
Muller RH, Jacobs C, Kayser O. Nanosuspensions as particulate drug formulations in therapy: Rationale for development and what we can expect for the future. Advanced Drug Delivery Reviews 2001;47(1):3-19.
Fichera, M.A., Wissing, S.A., Müller, R.H., Effect of 4000 bar homogenisation pressure on particle diminution on drug suspensions, Int. Meeting on Pharm., Biopharm. and Pharm. Technology, Nuremberg, 679-680, 2004.
Sucker, H., Hydrosole—eine Alternative für die parenterale Anwendung von schwer wasserlöslichen Wirkstoffen, in: Müller, R. H., Hildebrand, G. E., (Hrsg.), Pharmazeutische Technologie: Moderne Arznei-formen, 2. Auflage, 1998, WVG, Stuttgart.
Müller R.H., Heinemann, S. Surface Modelling of Microparticles as Parenteral Systems with High Tissue Affinity. In: Gurny, R., Juninger, H. E., ed. Bioadhesion—Possibilities and Future Trends: Wissenschaftliche Verlagsgesellschaft Stuttgart; 1989, 202-214.
Krause, K.P., et al., Heavy metal contamination of nanosuspensions produced by high-pressure homogenisation. Int J Pharm, 2000. 196(2): pp. 169-172.

* cited by examiner

Primary Examiner — Robert A Wax
Assistant Examiner — Bethany Barham
(74) Attorney, Agent, or Firm — Jeffrey S. Melcher; Manelli Selter PLLC (57) ABSTRACT

The invention concerns a method for producing ultrafine suspensions, characterized in that a substance in the form of a solid product at 20° C. is dissolved in a solvent, in that the solvent is very rapidly substantially drawn from said solution, in that the powder thus obtained, whereof the particles have an average particle-size distribution of the order of 1 to 50 μm (by laser diffractometry) is dispersed in a dispersing medium, and in that the resulting suspension is treated subsequently, using average to high forces, so as to obtain a suspension whereof the solid matter particles have a average particle-size distribution (by photon correlation spectroscopy) less than 3 μm, preferably less than 1 μm (1000 nm), and in particular less than 400 nm, more particularly still, less than 200 nm.

31 Claims, 2 Drawing Sheets

Figure 1:
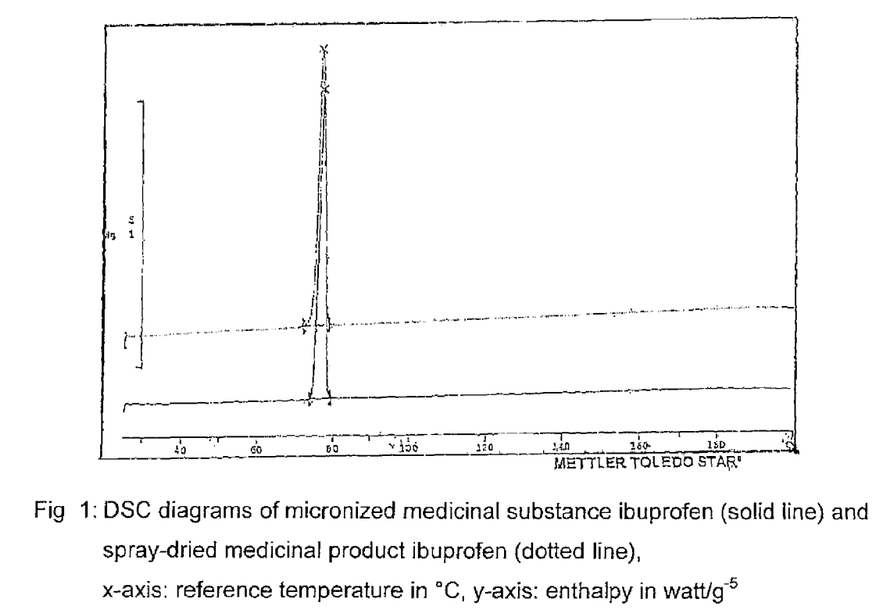

Fig 1: DSC diagrams of micronized medicinal substance ibuprofen (solid line) and spray-dried medicinal product ibuprofen (dotted line), x-axis: reference temperature in °C, y-axis: enthalpy in watt/g$^{-5}$ Fig 2: particle size distribution of micronized medicinal substance (solid line) and medicinal substance glibenclamide spray-dried according to the method (dotted line), measured by laser diffractometry after dispersal in aqueous solution of sodium dodecyl sulphate (SDS) 0.05% (m/m)

y-axis: percentage by volume, x-axis: particle diameter in μm

METHOD FOR PRODUCING ULTRAFINE SUBMICRONIC SUSPENSIONS

CROSS-REFERENCE TO RELATED APPLICATIONS

This application is a national stage entry under 35 U.S.C. 371 of International Application No. PCT/EP2006/002176, filed 9 Mar. 2006, designating the United States. This application claims foreign priority under 35 U.S.C. 119 and 365 to German Patent Application No. 10 2005 011 786.4, filed 11 Mar. 2005.

FIELD OF THE INVENTION

The invention describes a method for the production of ultra-fine suspensions in the submicron range for the fields of pharmacy, cosmetics, food production, agriculture and technical applications.

STATE OF THE ART

Approximately 40% of the pharmaceutical active ingredients which are in development or in clinical phases are poorly soluble, i.e. they belong to the class of the so-called problem drugs. Due to their poor solubility, these drugs have a very low bioavailability after oral administration, often the necessary therapeutic blood concentration levels cannot be reached. One alternative would be the intravenous administration of these drugs, but due to the poor solubility of the active ingredients the injection volumes required are so large that they cannot be administered in many cases. A traditional approach for these drugs is to increase their saturation solubility, e.g. by complexing (e.g. cyclodextrin inclusion compounds (Uekama K. Design, and Evaluation of Cyclodextrin-Based Drug Formulation. Chem. Pharm. Bull, Vol 52, 900-915 (2004) 2004; 52 (8): 900-15)) or—a very simple possibility—the use of injectable solvent mixtures (e.g. water-ethanol mixtures). But these approaches can be used for only a few drugs, as can be seen from the small number of products on the market which use these technologies (e.g. cyclodextrin compounds for parenteral application). One problem with these traditional approaches is that the molecule must "fit", i.e. for example the poorly-soluble drug molecule must fit into the cyclodextrin ring. This set of problems is increasingly gaining in importance at present, as the number of poorly soluble drugs is constantly increasing. There are estimates that approx. 60% of the drugs which come directly from synthesis are poorly soluble (Merisko-Liversidge E. Nanocrystals: Resolving Pharmaceutical Formulation Issues associated with poorly water-soluble Compounds. In: Marty J J, editor. Particles; 2002; Orlando: Marcel Dekker; 2002). In addition, many new active ingredients are poorly soluble in both water and organic solvents, which rules out from the outset the use of traditional formulation approaches, such as e.g. solvent mixtures. In addition, there are only a few organic solvents that are approved for parenteral administration, e.g. ethanol and propylene glycol. Most solvents have too high a toxicity.

The formulation approaches described above are relatively specific. The ideal solution would be a universal formulation approach which could be used for all poorly soluble active ingredients. Micronization is such a universal approach for perorally administered drugs which has already been in use for many years. The principle of micronization consists of an enlargement of the surface of the drug particles and the concomitant improvement in the dissolution rate. For this reason, micronization is a universal approach for all drugs of the biopharmaceutical specification class (BSC) class II (BSC II), i.e. for drugs which, although they permeate readily after peroral administration, have a clearly limited bioavailability due to a slow dissolution rate/low saturation solubility. Many newly developed drugs are so poorly soluble that the surface enlargement effected by micronization is not sufficient to increase the dissolution rate. In general, the dissolution rate is related to the saturation solubility (Noyes-Whitney law). The dissolution rate is proportional to the concentration gradient $(c_s-c_x)/h$ ($c_s$—saturation solubility, $C_x$—concentration in the ambient medium, h—thickness of the diffusion layer). This means that a very low saturation solubility generally results in a very low dissolution rate.

One consequence, in order to overcome the limits of micronization, was the move from micronization to nanosizing. The reduction of the particle size by a further dimension results in a clear surface enlargement and consequently an improved dissolution rate. The most varied methods are described for transferring micronized active ingredient crystals into the nanometer range, i.e. for producing nanocrystals.

Wet grinding with ball mills is used to reduce the size of drug crystals dispersed in surfactant solutions. The particle size of the "macrosuspension" is reduced by the grinding balls. One disadvantage of this technology is the possible contamination of the product by dust (grit) from the grinding balls (Buchmann S, Fischli, W., Thiel, F. P., Alex, R. Aqueous microsuspension, an alternative intravenous formulation for animal studies. In: 42nd Annual Congress of the International Association for Pharmaceutical Technology (APV); 1996; Mainz; 1996. p. 124). In addition, grinding times of hours or even days are required, depending on the hardness of the material to be ground. The achievable particle sizes, depending on the material to be ground, are typically less than 400 nm, and a particle size of 200-300 nm can often be achieved. However, to obtain particle sizes of approximately 100 nm, very long grinding times are required, which simultaneously involves a greater contamination of the product by grinding ball dust.

An alternative production method is the use of high-pressure homogenizers, i.e. methods that are based on the piston-gap principle or the jet-stream principle (microfluidizer technology, Microfluidics Inc. (U.S. Pat. No. 6,018,080)). The principle of the microfluidizer is that two beams strike each other at the front at very great speed, wherein the collision of the particles results in their comminution. A disadvantage of this method is that 50 or more cycles are required to achieve a small particle size. In addition, in the case of very hard, crystalline materials a relatively large proportion of particles greater than one μm in size remains. These particles do not then have the advantages of nanocrystals, such as the significantly increased dissolution rate with simultaneously increased saturation solubility. The advantage of the increased saturation solubility only becomes evident at a particle size smaller than approx. 1-2 μm (Mosharraf, M., Nyström, C., The effect of particle size and shape on the surface specific dissolution rate of micronised practically insoluble drugs. Int. J. Pharm., 122, 35-47, 1995). For this reason it is advantageous if more or less all particles have a size below this critical value.

In a piston-gap homogenizer, the macrosuspension is pressed through a very narrow gap which, depending on the pressure applied and on the viscosity of the dispersion medium, has a size of 5-20 μm (Rainer H. Müller, Jan Möschwitzer and Faris Nadiem Bushrab, Manufacturing of nanoparticles by milling and homogenization techniques, eds. Gupta, Kompella, Publisher: Marcel Dekker, submitted for printing). The high flow rate leads to cavitation forces, in addition particle collision and occurring shear forces likewise lead to a comminution of particles. The piston-gap homogenizers are used to homogenize particles dispersed in pure water/surfactant mixtures (U.S. Pat. No. 5,858,410), but they are also used to homogenize particles which are dispersed in non-aqueous media or in mixtures of water with water-miscible liquids (WO 0103670). The particle sizes achievable with piston-gap homogenizers are in the range of approx. 200-600 nm and in the case of very hard materials in the range of approximately 700-900 nm (Muller R H, Jacobs C, Kayser O. Nanosuspensions as particulate drug formulations in therapy: Rationale for development and what we can expect for the future. Advanced Drug Delivery Reviews 2001; 47 (1): 3-19). The production of pharmaceutical active ingredients in the range of approx. 100 nm with the help of the piston-gap homogenizers has not been described to date. The minimum achievable particle size depends on the hardness of the compounds, on the power density introduced and on the number of homogenization cycles. At a specific power density, the minimum particle size is achieved after a specific number of cycles. This is explained by the fact that during the comminution of the crystals they become more and more perfect, because crystals break primarily at defects and, with decreasing particle size, the number of defects is consequently constantly reduced. This leads to more perfect crystals which require ever greater applied force to be broken. After a specific number of homogenization steps at a specific power density, which power density is no longer sufficient to comminute the relatively perfect crystals further. The power density is measured by the applied homogenization pressure, this is typically in the range of 1000-1500 bar for the production of nanocrystals. There was an attempt to produce smaller nanocrystals by applying higher homogenization pressures of up to 4000 bar, but it was discovered that a further increase in the homogenization pressure has only a slight influence on the achievable particle size. There was only a relatively small reduction in particle size when the homogenization pressure was increased to 4000 bar (Fichera, M. A., Wissing, S A., Müller, R. H., Effect of 4000 bar homogenisation pressure on particle diminution on drug suspensions, Int. Meeting on Pharm., Biopharm. and Pharm. Technology, Nuremberg, 679-680, 2004). In this example, an increase in the homogenization pressure from 1500 to 4000 bar resulted in a reduction of only 165 nm in the particle size for every 1000 bar increase in pressure. In contrast, when the homogenization pressure was increased from 500 bar to 1500 bar, a reduction of 547 nm in the particle size was recorded. It seems that there is an exponential link between the required increase in power density and the achievement of a specific particle size. In addition, the wear of the machines used increases hugely, and such high pressures are therefore unsuitable for the industrial-scale production of nanocrystals. In summary, it can be established that—if the requirements in pharmaceutical production or in other fields are taken into account—the homogenization pressures should lie in the range of 1000-2000 bar. For this reason, new approaches had to be found to achieve smaller particle sizes. There is a prevailing opinion in the literature that an increase in the homogenization pressure is not a solution for achieving smaller nanocrystals, moreover all previously published data always only describe a particle size, achievable through homogenization, of over 200 nm.

A very old approach to the production of nanocrystals is precipitation, described in old pharmacopoeias as "via humida paratum" (produced by liquid route). The active ingredient is dissolved in a solvent, this solution is quickly added to a non-solvent (which is miscible with the solvent), wherein the active ingredient precipitates out.

In general, the particles are stabilized with surfactants or polymeric stabilizers. This principle was applied to produce the so-called "hydrosols" (U.S. Pat. No. 5,389,382). Later, some modifications of this precipitation principle were described (U.S. Pat. No. 6,251,945). But there are some problems associated with the precipitation principle. The main problem is to stabilize the precipitated crystals in the nanometer range. The nanocrystals attempt to grow and form microcrystals. One approach for preventing this is the immediate drying of the produced suspension, e.g. by lyophilization (Sucker, H., Hydrosole—eine Alternative für die parenterale Anwendung von schwer wasserlöslichen Wirkstoffen, in: Müller, R. H., Hildebrand, G. E., (eds.), Pharmaceutical Technologie: Moderne Arzneiformen, $2^{nd}$ edition, 1998, W V G, Stuttgart)). An alternative approach is the precipitation of particles with subsequent input of energy (e.g. by shear forces or ultrasound (U.S. Pat. No. 6,607,784). These forces can be applied e.g. by high-speed mixers or various high-pressure homogenizers (e.g. equipment from APV Gaulin, NiroSoavi, Avestin) or, where ultrasound is used, by equipment from Sonics. Treatment with forces results in a stabilizing of the produced particles, the crystals do not change in size during storage, unlike crystals which were not treated with shear forces. As a result, the same limitations apply to this method in respect of the minimum achievable particle size as for the above-described methods of high-pressure homogenization (U.S. Pat. No. 5,858,410/WO0103670). In addition, when using this precipitation method, it is necessary—at least in most cases—to remove the solvent. But in general every solvent is soluble at least to a certain extent in the non-solvent (e.g. water), which means that a certain residual content always remains in the water. In addition, the removal of the solvent can lead to an aggregation of the nanocrystals or even to particle growth. Therefore a comminution or production process which excludes the use of solvents would be desirable.

Drug nanocrystals have two particularly advantageous properties, firstly the increased saturation solubility and secondly the enlarged surface.

Both properties result in an increase in the dissolution rate according to the Noyes-Whitney law. In general it is advantageous to use nanoparticles that are as small as possible to achieve a maximum improvement in the oral bioavailability or a very rapid dissolution rate in the blood after intravenous administration. To produce such small nanoparticles with the methods known to date, a relatively large number of homogenization cycles is required. This is not advantageous for the production process. As small a number of cycles as possible is ideal to lower the production costs and minimize a contamination of the product with equipment dust. For this reason it would be advantageous to significantly lower the number of required cycles. Moreover, in the case of very hard drugs, a reduction in the particle sizes to the nanometer range has to date scarcely or not at all been possible. When using high-pressure homogenizers, relatively high pressures are applied, with the result that the wear of the equipment is also generally higher than when using low-energy equipment. For this reason, it would also be desirable if nanocrystals could also be produced with such low-energy equipment such as e.g. rotor-stator mixers or also with ball mills with a significantly reduced grinding time. All aspects listed have been realized in the present invention.

DESCRIPTION OF THE INVENTION

The present invention relates to a method which combines a very rapid drying step of a product followed by exposure to medium to high shear forces on this product. The active ingredient is dissolved in a suitable solvent in which it has a good solubility. The solvent can—but need not—contain additional substances such as e.g. surfactants, polymers, polymeric stabilizers, carbohydrates, electrolytes or non-electrolytes.

Examples of solvents are: N-methyl-2-pyrrolidone, 2-pyrrolidone, dimethyl acetamide, lactic acid, ethanol, methanol, isopropanol, acetone, chloroform, dichloromethane, dimethyl sulphoxide, N-propanol, glyerol, ethylene glycol, dimethyl formamide, dimethyl acetamide, organic acids (e.g. acetic acid, formic acid, fumaric acid).

In some cases it is desirable for the active ingredients which are poorly soluble in non-aqueous media to be present in nanocrystalline form. These active ingredients can be soluble in water, but are to be present dispersed in nanocrystalline form for their use in a non-aqueous medium. These active ingredients would be dissolved in water, the solution would be subjected to a very rapid drying step and this product would then be further processed in a non-aqueous medium in which the active ingredient has a low solubility.

Typical surfactants or stabilizing substances which can be added to the solvent are e.g. compounds from the range of poloxamers, poloxamines, ethoxylated mono- and diglycerides, ethoxylated lipids and lipoids, ethoxylated fatty alcohols and alkyl phenols, ethoxylated fatty acid esters, polyglycerin ethers and esters, lecithins, esters and ethers of sugars or sugar alcohols with fatty acids or fatty alcohols, phospholipids and sphingolipids, sterines, their esters or ethers, as well as their mixtures of these compounds. In addition, egg lecithin, soy lecithin or hydrogenated lecithins, their mixtures or mixtures of one or both lecithins with one or more phospholipid components, cholesterol, cholesterol palmitate, stigmasterine, other sterines, also come into consideration for addition to the solution.

Under certain circumstances, it can be necessary to add further substances to the solution in order to influence the properties of the solution itself or the properties of the dry powder produced from the solution. There come into consideration among others: diacetyl phosphate, phosphatidyl glycerol, saturated or unsaturated fatty acids, sodium cholate, peptization agents or amino acids and also cellulose ethers and esters, polyvinyl derivatives, alginates, xanthanes, pectins, polyacrylates, poloxamers and poloxamines, polyvinyl alcohol, polyvinyl pyrrolidone or glucose, mannose, trehalose, mannitol and sorbitol, fructose, sodium citrate, sodium hydrogen phosphate, sodium dihydrogen phosphate, sodium chloride, potassium chloride, calcium chloride, glycerin. If necessary, dyes, either in dissolved form or in undissolved form as pigments, can also be added to the solvent.

The concentrations of such components per component, based on the total weight of the solution, are preferably in the range of 1 to 90%, in particular 1 to 20% and preferably below 10%, ideally below 0.01 to 5%.

This solution, which can contain one or more active ingredients and one or more auxiliary substances, is then further processed. For this it is subjected to a very rapid drying process, for example with the help of a commercially available spray dryer. Examples of such spray dryers are equipment from Niro, Nubilosa, Caldyn, Büchi, APV, Trema etc.

Spray drying is known as a process which can be used for the processing of both thermolabile and thermostable active ingredients. Very temperature-sensitive substances can also be processed in particular by using solvents with a low boiling point.

In contrast to the spray-drying methods described in the literature for producing small and very small particles (U.S. Pat. No. 6,565,885; U.S. Pat. No. 6,696,084, PCT/US00/34606), the material obtained here is further processed by the use of shear forces. These shear forces result in a product in the nanometer range which simultaneously has a relatively small particle size distribution.

In the case of oxidation-sensitive substances, both the drying process and the following use of the shear forces can take place under a protective atmosphere.

Alternatively, e.g. fluidized-bed dryers (e.g. equipment from Niro) or other equipment (such as e.g. thin-layer vacuum dryers or dry roller dryers) which result in a very rapid drying by removing the solvent can also be used. It is necessary merely that the solvent removal take place relatively quickly.

In general it is to be noted that the medium to high forces applied according to the invention are shear, cavitation, grinding and/or ultrasound forces, in particular high-pressure homogenizers, jet-stream devices, rotor-stator colloid mills, ball mills, tooth-wheel mixers, high-shear mixers or ultrasound apparatuses, wherein the equipment used preferably operates at a power density of $10^3$ to $10^{13}$ W/m$^3$, in particular $10^6$ to $10^{13}$ W/m$^3$, wherein the medium forces preferably range from $10^6$ to $10^7$ or $10^8$ W/m$^3$ and the high forces are preferably in the range of $10^9$ or $10^{10}$ to $10^{12}$ or $10^{13}$ W/m$^3$.

The method according to the invention is characterized in that the solvent removal/the drying of the proportion in the drying process of produced solution takes place within 5 seconds, preferably within 2, in particular 1, more preferably 0.5, and even more preferably within 0.1 seconds.

The method according to the invention is further characterized by the fact that the solvent removal/the drying results in a residual solvent content/residual humidity of at most 10 wt. %, preferably 5 wt. %, more preferably 1 wt. %, in particular 0.5 wt. %, more particularly 0.1 wt. % or less.

The active ingredients to be processed can come from the most varied fields, i.e. pharmaceutical active ingredients, cosmetic active ingredients, but also additives for the food industry and materials for other technical fields can be processed, which are preferably to be present as nanocrystalline material, such as e.g. dyes and colour pigments for paints and varnishes or for cosmetic uses.

Pharmaceutical active ingredients can come from the therapeutic fields listed below (optionally in their poorly water-soluble form, e.g. as base instead of the hydrochloride):

Examples of drug groups to be processed in the form of a nanosuspension are:

1. Analgesics/antirheumatics e.g. morphine, codeine, piritramide, fentanyl, levomethadone, tramadol, diclofenac, ibuprofen, dexibuprofen, ketoprofen, dexketoprofen, meloxicam, indomethacin, naproxen, piroxicam, rofecoxib, celecoxib, 2. Antiallergics e.g. pheniramine, dimethindene, terfenadine, astemizole, loratidine, desloratadine, doxylamine, meclozine, fexofenadine, mizolastine 3. Antibiotics/chemotherapeutics e.g. rifamycin, ethambutol, thiazetazone, buparvaquone, atovaquone, tarazepide 4. Antiepileptics e.g. carbamazepine, clonazepam, mesuximide, phenytoin, valproic acid 5. Antimycotics
   a) internal:
      e.g. natamycin, amphotericin B, miconazole, itraconazole
   b) external plus:
      e.g. clotrimazole, econazole, fenticonazole, bifonazole, ketoconazole, tolnaftate
6. Corticoids (internal)
   e.g. aldosterone, fludrocortisone, betametasone, dexametasone, triamcinolone, triamcinolonacetonide, fluocortolone, hydrocortisone, hydrocortisonacetate, prednisolone, prednylidene, cloprednol, budesonide, methylprednisolone
7. Dermatics
   a) Antibiotics:
      e.g. tetracycline, erythromycin, framycetin, tyrothricin, fusidic acid
   b) Virustatics as above, plus:
      e.g. vidarabine
   c) corticoids as above, plus:
      e.g. amcinonide, fluprednidene, alclometasone, clobetasol, halcinonide, fluocinolone, clocortolone, flumetasone, diflucortolone, fludroxycortide, halometasone, desoximetasone, fluocinolide, fluocortinbutyl, fluprednidene, prednicarbate, desonide
8. Hypnotics, sedatives
   e.g. cyclobarbital, pentobarbital, methaqualone, benzodiazepines (flurazepam, midazolam, nitrazepam, lormetazepam, flunitrazepam, triazolam, brotizolam, temazepam, loprazolam)
9. Immunotherapeutics and cytokines
   e.g. azathioprine, ciclosporin
13. Local anaesthetics
   a) internal:
      e.g. butanilicaine, mepivacaine, bupivacaine, etidocaine, lidocaine, articaine
   b) external plus:
      e.g. oxybuprocaine, tetracaine, benzocaine
10. Anti-migraine agents
   e.g. lisuride, methysergide, dihydroergotamine, ergotamine, triptanes (such as e.g. zolmitriptane, sumatriptane, rizatriptane)
11. Narcotics
   e.g. methohexital, propofol, etomidate, ketamine, thiopental, droperidol, fentanyl
12. Parathyroid gland hormones, calcium metabolism regulators
   e.g. dihydrotachysterol
13. Ophthalmic agents
   e.g. cyclodrine, cyclopentolate, homatropine, tropicamide, pholedrine, edoxudine, aciclovir, acetazolamide, diclofenamide, carteolol, timolol, metipranolol, betaxolol, pindolol, bupranolol, levobununol, carbachol
14. Psychopharmacological agents
   e.g. benzodiazepines (lorazepam, diazepam), clomethiazole
15. Sexual hormones and their inhibitors
   e.g. anabolics, androgens, antiandrogens, gestagens, estrogens, anti estrogens
16. Cytostatic agents and metastasis inhibitors
   a) alkylating drugs such as melphalan, carmustine, lomustine, cyclophosphamide, ifosfamide, trofosfamide, chlorambucil, busulfan, prednimustine, thiotepa
   b) antimetabolites such as fluorouracil, methotrexate, mercaptopurine, tioguanine
   c) alkaloids such as vinblastine, vincristine, vindesine
   d) antibiotics such as dactinomycin
   e) taxol and related or analogous compounds
   f) dacarbazine, estramustine, etoposide Pharmaceutical active ingredients of particular interest are oxaliplatin, paclitaxel, taxane, ketoconazole, itraconazole, ibuprofen, naproxen, omeprazole, pantoprazole, loratadine, desloratadine, loperamide, daglutril.

The thus-obtained dry powders which were produced according to the method described above have a particle size in the range of ca. 1 µm to 10 µm, sometimes up to approximately 30-50 µm. In most cases, the obtained product is crystalline or almost crystalline (Examples 8-11). Depending on the chemical properties and the melting point of the active ingredients, the dry product can also be partly amorphous or amorphous.

The obtained powder is then dispersed in a non-solvent by means of conventional stirring methods, e.g. by a high-speed stirring disk. The stirring forces to be applied are relatively small and are to be just sufficient to convert the dry product into a suspension. If necessary, the particles can be stabilized by adding surfactants, anti-flocculants (e.g. sodium citrate) and polymeric stabilizers, as already described above. One or more substances of the above-named examples can therefore be added to the solution to be produced from the powder, in order to influence the particle dispersions as desired.

Medium or high shear and/or cavitation forces are then applied to the thus-produced suspensions. Medium shear forces can be applied by rotor-stator stirring systems (power density: $10^6/10^7$ W/m$^3$) or alternative equipment such as e.g. tooth wheels. Alternatively, equipment with a higher power density in the range of $10^9/10^{13}$ W/m$^3$ can be used with the help of which high forces can then be applied to the suspensions. Examples of such equipment are jet homogenizers or piston-gap homogenizers (e.g. equipment from the Avestin, APV Gaulin, Niro Soavi) series or ultrasound generators from Sonics.

Methods that are described in the literature, such as e.g. the hydrosol method (Sucker, H., Hydrosole—eine Alternative für die parenterale Anwendung von schwer wasserlöslichen Wirkstoffen, in: Müller, R. H., Hildebrand, G. E., (eds.), Pharmazeutische Technologie: Moderne Arzneiformen, 2$^{nd}$ edition, 1998, W V G, Stuttgart) and the microprecipitation method (U.S. Pat. No. 6,607,784) require the solvent used to dissolve the active ingredient to be miscible with the dispersion medium used for the production of the nanosuspension. These preconditions need not be satisfied with the invention described here, as almost any solvent in which the active ingredient to be processed can be dissolved can be used. The solvent used need not be miscible with the dispersion medium to produce the nanosuspension. In addition, this also opens up the possibility of using relatively toxic solvents such as e.g. chloroform or dimethyl sulphoxide, as these can be removed very efficiently by or after the rapid drying process. The remaining residual concentrations move in the lower ppm range and are diluted still further during the production of the nanosuspension. This leads to a much lower overall solvents contamination than is possible when using previously known methods.

Nanocrystalline material was not obtainable using high-pressure homogenization on an aqueous suspension of the drug ibuprofen. The particle size which was measured with the help of photon correlation spectroscopy was 1172 nm (Example 1). Even an increase in the number of cycles to 60 homogenization cycles led only to a negligibly lesser comminution to 1150 nm. This means that with relatively hard materials it is not possible to readily produce drug nanocrystals when using the previously known methods. Ibuprofen was then produced using the method according to the invention. For this, it was spray-dried (Example 8) and the spray-dried powder dispersed in surfactant solution (Example 2). After only 20 homogenization cycles, drug nanocrystals 636 nm in size were obtained. The polydispersity index (PI) of 0.169 showed a relatively narrow particle size distribution which was in the range of emulsions for parenteral feeding (Müller R. H., Heinemann, S. Surface Modelling of Microparticles as Parenteral Systems with High Tissue Affinity. In: Gurny, R., Juninger, H. E., ed. Bioadhesion—Possibilities and Future Trends: Wissenschaftliche Verlagsgesellschaft Stuttgart; 1989, 202-14). The use of the invention thus led to a halving of the achieved particle size compared with known methods for an identical or similar number of cycles.

Larger nanocrystals are preferred for certain applications, e.g. to achieve extended blood levels after peroral application. Nanocrystals that are too fine would dissolve too fast, for which reason nanocrystals in the upper nanometer range are sometimes preferred. With the process shown here, it was possible to produce nanocrystals 930 nm in size within 5 homogenization cycles (Example 2). This is very advantageous for an industrial-scale production.

It is posited in the literature that particle size reduction occurs more often using amorphous substances as starting material. But the spray-dried ibuprofen used here was clearly crystalline (Example 3) according to the Differential Scanning Calorimetry (DSC) results.

For this reason, the surprising efficiency of the particle size reduction cannot be due to the use of an amorphous starting material.

Figure 2:
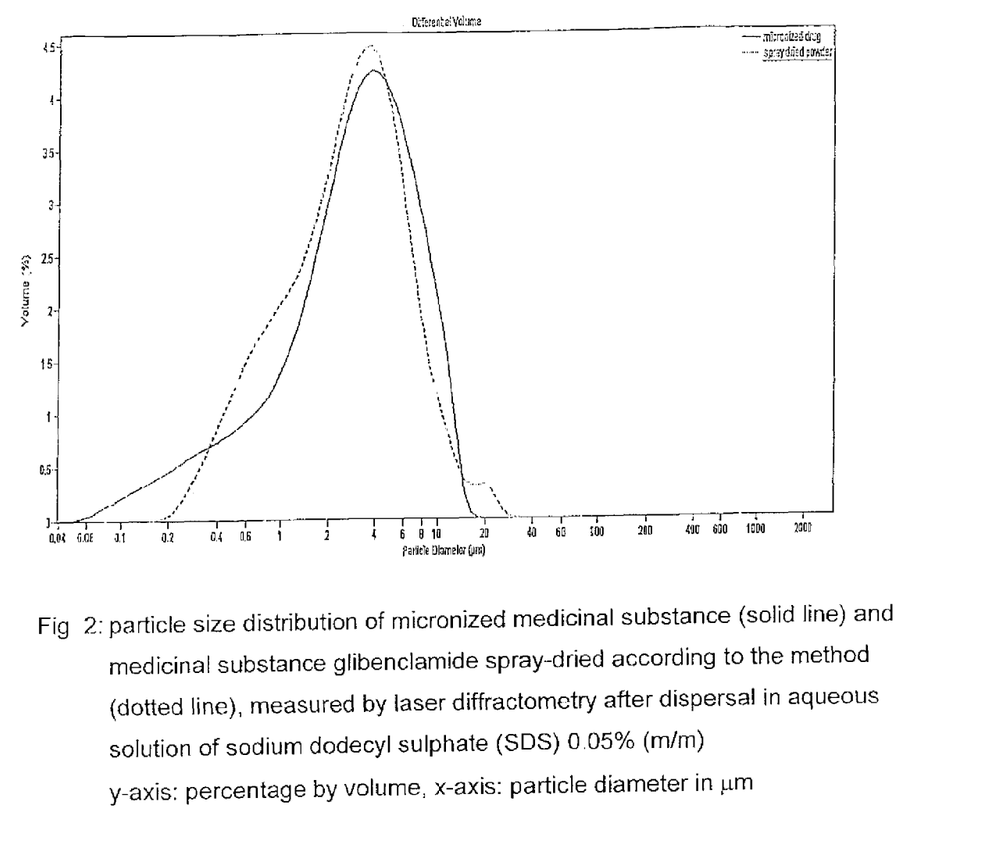

It is furthermore described in the literature that the use of micronized starting material favours particle size reduction, i.e. results in smaller particles after fewer homogenization cycles. The particle size of the glibenclamide used for the spray-drying was analyzed (Example 6), and this powder was then dissolved in ethanol (96% v/v) and spray-dried. The particle size of this spray-dried powder was investigated again. Laser diffractometry was used to measure particle size. For this, the dry powder, both the starting material and the spray-dried product, were dispersed in surfactant-containing water and analyzed with the help of a Coulter LS 230 (Coulter Electronics, USA). FIG. 2 in Example 6 shows that the particle size distributions of the two powders are almost identical. For this reason, the surprising particle size reduction which occurs with the new process cannot be explained by a different size of the starting material. In summary, it can be established that neither an amorphous character of the starting material nor a smaller size of the starting material played a part. These factors do not account for the achieved comminution effects.

Glibenclamide was first produced according to the already-known method (U.S. Pat. No. 5,858,410) (Example 4, batch Glb-A). For this, the powdered starting material was dispersed in a surfactant solution (contained 1% poloxamer 188 and 0.2% sodium dodecyl sulphate (SDS) w/w) and homogenized with 20 cycles at 1500 bar with a Micron LAB 40 (APV Gaulin, Germany). The PCS diameter was 1106 nm and the PI of 0.545 indicates a very broad particle size distribution. The use of the new method (Example 4 Glb-B) under the same conditions resulted in drug nanocrystals with a PCS diameter of 406 nm and a polydispersity index of 0.264 after only one homogenization cycle. This means that, despite the use of many homogenization cycles with the traditional method, the product lies outside the nanometer range and has a broad particle size distribution. The use of a single homogenization cycle which simultaneously results in a halving of the particle size is naturally very suitable for production.

The pharmaceutical active ingredient hydrocortisone acetate was processed conventionally by homogenizing it in a surfactant solution (1% poloxamer 188 and 0.2% SDS w/w) at 1500 bar with 20 cycles. Drug nanocrystals with a PCS diameter of 716 nm and a PI of 0.45 were obtained (Example 7). The use of the method described here (Example 7 Hca-B) resulted in a particle size of 476 nm and a PI of 0.170 after only 10 homogenization cycles. Again, a particle size distribution was thus achieved such as is described for parenteral fatty emulsions.

Drug nanocrystals were also produced in dispersion media composed of water and substances miscible with water. If the drug hydrocortisone acetate is processed in a mixture of water:glycerol (50:50 w/w) by the method according to the invention, a particle size of 637 nm is obtained after 30 homogenization cycles (Example 12).

It is of particular interest for oral administration to produce drug nanocrystals in non-aqueous media such as e.g. polyethylene glycols (PEGs) or various natural or synthetic oils and fats (e.g. medium chain triglycerides—MCT). These suspensions can then be filled directly into hard or soft gelatine capsules.

The drug amphotericin B was likewise processed using the method according to the invention. For this, a spray-dried drug was dispersed in a surfactant solution (0.5% Tween 80) in PEG 300 and then homogenized for 15 cycles at 1500 bar. A particle size of LD 50% 172 nm and LD 99% of 658 nm was achieved (Example 13).

High-pressure homogenizers or more generally equipment with a high power density are subject to greater equipment wear than equipment with smaller power density. Despite the fact that high-pressure homogenizers result in only a non-critical product contamination even under particularly severe conditions (Krause, K. P., et al., Heavy metal contamination of nanosuspensions produced by high-pressure homogenisation. Int J Pharm, 2000. 196(2): pp. 169-72)), it is desirable in general to be able to use equipment with a lower power density in order to achieve particles in the nanometer range.

Spray-dried glibenclamide was dispersed in an aqueous surfactant solution (1% poloxamer and 0.2% SDS) and treated with an Ultra-Turrax (Janke & Kunkel) for 1 minute at 20,000 rpm. A particle size of 961 nm was already achieved thereby (Example 14).

The particle size measurement was carried out using laser diffractometry (LD) and photon correlation spectroscopy (PCS). The laser diffractometry was carried out with a Coulter LS 230 (Beckman-Coulter, USA) and delivers a volume-related particle size distribution as a result. The parameters used for measurement were the 50% (LD 50%) and LD 99% diameters. LD 50% means that 50% of the particles have a diameter below the given value relative to their volume. The PCS analysis was carried out with a Zetasizer 4 (Malvern Instruments, GB). The PCS gives an average particle diameter (z average) of the main population and a polydispersity index (PI) as a measure of the breadth of the particle size distribution. The PI for relatively narrow distributions is between 0.1-0.2, and values greater than 0.5 and higher indicate a very broad particle size distribution.

Differential Scanning Calorimetry (DSC) was carried out with a Mettler Toledo DSC 821 (Mettler Toledo, Germany). The heating-up rate was 5 K/min.

The invention is characterized in that particulate material in the nanometer range can be achieved by using a relatively small number of homogenization cycles or by a relatively short exposure to shear and cavitation forces. After only 1-5 cycles, the particle diameters are normally below 1000 nm, very often below 800 nm and, in the case of softer materials, below 700 nm. An increase in the number of cycles results in particles with a particle size of less than 500 nm and with a higher numbers of cycles 300-400 nm can be achieved. With a larger number of cycles, in particular if the homogenization pressure is increased from 1500 bar to 2000 bar, values of less than 200 nm can be achieved, in some cases values of even less than 100 nm.

The production of pharmaceutical active ingredients in the nanometer range is advantageous for the most varied application routes. In topical preparations for applications to the skin, nanocrystalline forms increase the saturation solubility, which leads to an improved penetration into the skin. After oral administration, the dissolution rate is improved. The increased saturation solubility leads to an increased concentration gradient, which in turn leads to increased blood concentration levels. Parenteral administration via an intravenous injection is also possible, wherein the rapidly-dissolving nanocrystals imitate the injection of a solution. The injection into visceral cavities or intramuscular administration creates depots which result in extended blood levels compared with intravenous application. A further use for drug nanocrystals would be e.g. the administration at or in the eye, which results in an extended residence time of the active ingredient at the eye. Drug nanocrystals can be positively charged by the use of suitable surfactants or stabilizers, which results in an increased adhesivity to the skin and to products attached to the skin such as e.g. hairs. A particle size in the nanometer range is also advantageous e.g. for the food industry, as auxiliary substances can be distributed much better in the food, e.g. additives in baking. Nanocrystalline dyestuffs improve the colouring effect and the colour intensity of cosmetic products, but also of colours for various other uses. Nanocrystalline material is also of interest for the textile industry (e.g. to produce materials which have a high adhesivity to textile fibres, particularly when they are countercharged relative to the textile fibre).

The invention therefore describes quite generally a process to produce nanoparticles in a very effective manner using a combination of a rapid drying process followed by use of medium or high shear forces. The active ingredient is dissolved in a solvent, auxiliary substances such as surfactants, polymers, carbohydrates and other different auxiliary substances can be added to this solution. The auxiliary substances can be soluble in the solvent used or alternatively be present dispersed in same in particulate form. This liquid containing the active ingredient in dissolved form is then dried or spray-dried using conventional drying equipment (e.g. spray dryers, fluidized-bed dryers, dry roller dryers, thin-layer vacuum dryers). The obtained powder is then dispersed in a liquid medium which can be water, a mixture of water and liquids miscible in water or a non-aqueous liquid. The dispersion medium can contain e.g. surfactants, polymeric stabilizers or other additives. The formed dispersion is then exposed to medium shear forces (e.g. rotor-stator mixers, tooth wheels) or alternatively high shear and/or cavitation forces using high-pressure homogenizers (jet-stream homogenizers, piston-gap homogenizers) or ball mills. Other equipment which can exert high forces (such as e.g. cavitation or ultrasound) on the particles can also be used. The applied forces result in a reduction of the particle size into the nanometer range. The described method is characterized in that much less energy is required than in the previously described methods for the production of nanocrystals and in that many fewer homogenization cycles are required when using high shear and cavitation forces. Both factors are advantageous, as a product contamination due to equipment wear is reduced. In addition, production costs are reduced due to much faster production due to the reduced number of homogenization cycles required. For active ingredients the particle size of which was hitherto not, or scarcely, reducible to the nanometer range using an acceptable number of cycles, the described method represents the only production possibility for the production of nanoparticles.

The obtained nanoparticles can be used in different fields, e.g. in the pharmaceutical field, in the cosmetics industry, the food industry, the textiles industry and other technical fields.

In other words, the present invention describes a process for the production of pharmaceutical, cosmetic or other active ingredients in nanoparticulate form, i.e. the particles have an average size of less than 1000 nm. The active ingredient is dissolved in a solvent to which different auxiliary substances can optionally be added, and then quickly dried. The dry product is dispersed in a dispersion medium and the obtained suspension then subjected to medium or high forces (e.g. ultrasound, cavitation and/or shear forces, e.g. produced by high-pressure homogenizers), which results in a particle size reduction to the nanometer range. The obtained nanosuspensions serve either independently as a product or are further processed.

The following examples are intended to illustrate the invention.

EXAMPLE 1

A nanosuspension with the active ingredient ibuprofen was produced according to the known method (batch Ibu-A). For this, 0.4 g micronized ibuprofen was dispersed for 1 minute in 39.6 g of an aqueous surfactant solution which contained 0.08 g sodium dodecyl sulphate (SDS) and 0.4 g poloxamer 188 with an Ultra-Turrax (Janke & Kunkel, Germany) at 9,500 rpm. Homogenization was then carried out with a Micron LAB 40 high-pressure homogenizer (APV-Homogenisers, Unna, Germany). Initially, 2 cycles at 150 bar were carried out, then 2 cycles at 500 bar, then further homogenization was carried out at 1500 bar. After 40 homogenization cycles at room temperature (RT) and a pressure of 1500 bar, an average particle diameter of 1172 nm and a polydispersity index (PI) of 0.270 were recorded for batch Ibu-A with the help of photon correlation spectroscopy (PCS). A further increase in the number of cycles to 60 cycles resulted in a further, not noteworthy, reduction in the average particle size (according to PCS) to only 1150 nm.

EXAMPLE 2

Nanosuspension batch Ibu-B was produced using the method according to the invention. For this, firstly 20 g micronized ibuprofen was dissolved in 180 g ethanol (96% v/v) and this solution spray-dried with a Mini Spray Dryer spray dryer, model 190 (Büchi, Switzerland). The spray-drying conditions were: volumetric flow rate 600 l/min, pump setting 6, aspiration 3-4, heating rate: 3-4, inlet temperature: 72-76° C., outlet temperature: 58-60° C. The thus-obtained drug powder was further processed in the same formulation composition and under identical conditions (as given under Ex. 1). After only 20 homogenization cycles at 1500 bar, an average particle diameter of 636 nm with a PI of 0.169 was recorded by means of PCS. After only 5 cycles, particle sizes of 930 nm with a PI of 0.350 were measured by PCS.

EXAMPLE 3

FIG. 1 shows examinations of the crystalline state of the starting materials used for the production of the batch Ibu-A (conventional) and batch Ibu-B (produced according to the invention, as mentioned in Example 2) which were carried using Differential Scanning Calorimetry (DSC). The micronized starting substance had an extrapolated melting point of 76.60° C. and a normalized enthalpy of fusion of 124.99 J/g. The spray-dried ibuprofen powder produced according to the conditions mentioned under Example 2 had an extrapolated melting point of 76.14° C. and a normalized enthalpy of fusion of 117.04 J/g. It can be established by means of this example that the starting materials of batch A and B do not differ in respect of their crystallinity, with the result that the improved effectiveness during homogenization is not attributable to a decrease in crystallinity.

EXAMPLE 4

For Example 4, two nanosuspensions with the active ingredient glibenclamide were produced for the purpose of comparison. Batch Glb-A was produced according to the known method (batch size 40 g, 0.4 g glibenclamide, 0.08 g SDS, 0.4 g poloxamer 188, 39.12 g water; production conditions as given under Example 1), batch Glb-B using the method according to the invention. For this, 5 g glibenclamide together with 1 g SDS were dissolved in 794 g ethanol (96% v/v) and spray-dried with a Mini Spray Dryer spray dryer, model 190 (Büchi, Switzerland). The spray-drying conditions were: volumetric flow rate 600 l/min, pump setting 10, aspiration 4, heating rate: 4-5, inlet temperature: 90° C., outlet temperature: 58-60° C. To produce the active ingredient dispersion, 480 mg of the spray-dried powder was dispersed in 39.52 g of an aqueous solution which contained 0.4 g poloxamer 188 according to the method given under Example 1 and then high pressure homogenized, as likewise given in Example 1, by means of a Micron LAB 40. For batch Glb-A, an average particle size of 1106 nm at a PI of 0.545 was obtained by PCS after one homogenization cycle at 1500 bar. In contrast, batch Glb-B already showed a size of 506 nm at a PI of 0.385 after the first homogenization cycle. It is shown therefore that with the method according to the invention a single homogenization step is sufficient to obtain particles with an average diameter in the nanometer range. Furthermore, the suspensions obtained according to the new method show a more homogeneous particle size distribution.

EXAMPLE 5

The suspensions produced for Example 4 were used to examine what influence the method according to the invention has on the required number of cycles to reach the limit dispersity. While 40 homogenization cycles were required for batch Glb-A according to the known method to obtain an average particle size of 500 nm at a PI of 0.25, 15 cycles were already sufficient for the batch Glb-B produced according to the invention to obtain particle sizes of 431 nm at a PI of 0.250. 20 cycles in the case of Glb-B resulted in an average particle diameter of 406 nm at a PI of 0.264. A decisively increased effectiveness in the production of nanosuspensions thereby results, as on the one hand the required number of cycles can be markedly reduced and on the other hand the introduced power density leads to much smaller particles.

EXAMPLE 6

To rule out a difference in the particle size of the starting material as a cause of the markedly improved results in respect of the particle size of batch Glb-B from Example 5, the volume-based particle size distribution of both starting materials was measured for the high pressure homogenization process using laser diffractometry. For this, the powders were each dispersed in an aqueous SDS solution (0.05% SDS) by stirring and then measured as a suspension with a Coulter LS 230. FIG. 2 shows that there is no significant difference between normally micronized starting material and the powder produced according to the invention by spray-drying (according to Example 4), with the result that a changed size of the starting material can be ruled out as a major cause of the improved effectiveness.

EXAMPLE 7

Two nanosuspensions with the active ingredient hydrocortisone acetate were produced. Batch Hca-A was produced as given under Example 1 (same formulation and production conditions) according to the known method, batch Hca-B using the method according to the invention. For this, 3 g hydrocortisone acetate and 3 g poloxamer 188 were dissolved in 794 g ethanol (96% v/v) and then spray-dried with a Mini Spray Dryer spray dryer, model 190 (Büchi, Switzerland). The spray-drying conditions were: volumetric flow rate 600 l/min, pump setting 12, aspiration 3-4, heating rate: 3-4, inlet temperature: 90° C., outlet temperature: 58-60° C. The thus-obtained powder was then used further for the production of batch Hca-B. For batch Hca-A, an average particle size of 716 nm at a PI of 0.450 was obtained after 20 homogenization cycles. Batch Hca-B was produced in basically the same way as batch Hca-A, but 800 mg of the spray-dried powder was dispersed in 40 g of an aqueous solution of 0.08 g SDS and then further processed according to the conditions mentioned under Example 1 for the homogenization process. In contrast to batch Hca-A, batch Hca-B showed a size of 476 nm at a PI of 0.170 after only 10 homogenization cycles. Thus it is shown that with the method according to the invention, a small number of homogenization steps is sufficient to obtain nanosuspensions which have a particle size distribution in the range of parenteral fatty emulsions.

EXAMPLE 8

Ibuprofen spray-dried according to the invention, produced as mentioned in Example 2, has a crystalline appearance and a particle size distribution of approx. 1-5 µm in the 1000× magnification microscope picture. Macroscopically, it is a white, loose powder with likewise crystalline appearance.

EXAMPLE 9

Ibuprofen spray-dried according to the invention, produced as mentioned in Example 2 but with 0.2% SDS added to the solution, has a crystalline appearance and a particle size distribution of approx. 1-5 µm in the 1000× magnification microscope picture. The particles are overall somewhat smaller than in the example without the addition of surfactant. Macroscopically, this is a white, loose powder with likewise crystalline appearance.

EXAMPLE 10

Glibenclamide spray-dried according to the invention, produced as mentioned in Example 4 but with no added surfactant in the solvent, has a very regular, uniformly round appearance and a particle size distribution of approx. 2-4 µm in the 1000× magnification microscope picture. Macroscopically it is a white powder with a strong electrostatic charge.

EXAMPLE 11

Glibenclamide spray-dried according to the invention, produced as mentioned in Example 4, likewise has a very regular, uniformly round appearance and a particle size distribution of approx. 2-4 μm in the 1000× magnification microscope picture. Macroscopically it is likewise a white powder with a strong electrostatic charge.

EXAMPLE 12

Hydrocortisone acetate was treated in a mixture of water:glycerol (50:50 w/w) using the method according to the invention. For this, a spray-dried drug powder was produced according to Example 7 batch Hca-B, 0.8 g of this powder was dispersed in 39.2 g of a water:glycerol mixture (50:50 w/w) and subjected to a high pressure homogenization process corresponding to the method given under Example 1. After 30 homogenization cycles, the average particle size measured by PCS was 637 nm.

EXAMPLE 13

The drug amphotericin B was likewise processed using the method according to the invention. Spray-dried drug powder was produced by dissolving 0.2 g amphotericin B in 10 g dimethyl sulphoxide (DMSO), adding this solution to 189.8 g methanol and then spray-drying this solution with a Mini Spray Dryer spray dryer, model 190 (Büchi, Switzerland). The spray-drying conditions were: volumetric flow rate 600 l/min, pump setting 10, aspiration 3, heating rate: 1, inlet temperature: 56° C., outlet temperature: 34° C. The thus-obtained powder was dispersed in PEG 300 with the addition of 0.5% Tween 80 and then homogenized at 1500 bar with a Micron LAB 40 (APV-Homogenisers, Unna, Germany), as mentioned under Example 1. The particle sizes measured by laser diffractometry were 172 nm (LD 50%) and 658 nm (LD 99%).

EXAMPLE 14

Spray-dried glibenclamide (from Example 4) was dispersed in an aqueous surfactant solution (1% poloxamer) and treated with a T 25 Ultra-Turrax (Janke & Kunkel, Germany) for 1 minute at 20,000 rpm. A particle size of 961 nm measured by PCS was already achieved thereby.

A poorly soluble substance within the meaning of the invention has a maximum solubility of 1%, preferably less than 0.1% and in particular less than 0.01%, relative to the weight of the solvent/dispersing agent in the respective solvent/dispersing agent.

The invention claimed is:

1. Method for the production of ultra-fine suspensions comprising: dissolving a substance which is a solid at 20° C. in a solvent to form a solution; very rapidly and substantially removing the solvent from said solution to obtain a powder comprising particles of which have an average particle size in the range of 1 to 50 μm (according to laser diffractometry); dispersing the powder in a dispersing medium to obtain a suspension; and further processing the suspension by applying medium to high mixing forces to form a suspension comprising solid particles of which having an average particle size (according to photon correlation spectroscopy (PCS)) below 1 μm; wherein the polydispersity index of the resulting particle is decreased and wherein the substance is a medical drug, cosmetically active agent, an additive for food, a dye or a pigment.

2. The method according to claim 1, wherein the solid particles having an average particle size of below 400 nm.

3. The method according to claim 1, wherein the solid particles having an average particle size of below 200 nm.

4. The method according to claim 1, wherein the medium to high mixing forces are shear forces, cavitation forces, milling forces and/or ultrasonic forces, applied by at least one device comprising high pressure homogenizer, jet stream devices, rotor-stator colloid mills, ball mills, tooth wheel mixers, high shear mixers or ultrasonic devices, wherein the device used works with a power density of $10^3$ to $10^{13}$ W/m$^3$.

5. The method according to claim 1, wherein the solvents used for dissolution are water, mixtures of water with completely water miscible or partially water miscible liquids or hydrophilic liquids.

6. The method according to claim 1, wherein the solution to be produced first or the suspension containing the particles to be comminuted also contains one or more further auxiliary substances and dispersion stabilizing substances, wherein the concentration of such components per components is, based on the total weight of the solution, in the range of 1 to 90%.

7. The method according to claim 6, wherein the stabilizing substances comprise compounds of the group of poloxamers, poloxamines, ethoxylated mono- and diglycerides, ethoxylated lipids and lipoids, ethoxylated fatty alcohols and alkyl phenols, ethoxylated fatty acid esters, polyglycerinethers and -esters, lecithins, esters and ethers of sugars or sugar alcohols with fatty acids or fatty alcohols, phospholipids and sphingolipids, sterols, their esters or ethers, as well as mixtures of such compounds.

8. The method according to claim 6, wherein the stabilizing substances comprise egg lecithin, soy lecithin or hydrogenated lecithin, their mixtures or mixtures of one or both lecithins with one or more phospholipid components, cholesterol, cholesterol palmitate, stigmasterol, other sterols, or mixtures thereof.

9. The method according to claim 6, wherein the stabilizers comprise diacethyl phosphate, phosphatidyl glycerol, saturated or unsaturated fatty acids, sodium cholate, peptization agents, amino acids, or mixtures thereof.

10. The method according to claim 6, wherein the solution contains a viscosity increasing substance selected from the group consisting of cellulose ethers and esters, polyvinyl derivatives, alginates, xanthanes, pectines, polyacrylates, poloxamers or poloxamines, polyvinyl alcohol, polyvinyl pyrrolidone, or mixtures thereof.

11. The method according to claim 6, wherein the solution also contains an auxiliary substance selected from the group consisting of glucose, mannose, trehalose, mannitol and sorbitol, fructose, sodium citrate, sodium hydrogen phosphate, sodium dihydrogen phosphate, sodium chloride, potassium chloride, calcium chloride, glycerin, dyes or pigments.

12. The method according to claim 9, wherein the solvent removal/the drying is effected by use of a spray dryer.

13. The method according to claim 1, wherein the solvent removal/the drying is effected by use of fluidized bed dryer, dry roller dryer, thin layer vacuum dryer, or other dryers or drying methods, which result in a rapid removal of solvent.

14. The method according to claim 1, wherein the solvent removal/the drying of the part of the obtained solution, which is present in the drying process, occurs within 5 seconds.

15. The method according to claim 1, wherein the solvent removal/the drying results in a residual solvent content/residual humidity of at maximum 10 wt. %.

16. The method according to claim 1, wherein the powder obtained after the solvent removal is crystalline, partially crystalline or amorphous.

17. The method according to claim 1, wherein the powder obtained after the solvent removal is dispersed in a dispersing agent by way of stirring using blade stirrers, rotor-stator systems, static mixers, optionally additional passage through a rotor-stator colloid mill, so that a suspension is obtained.

18. The method according to claim 17, wherein as dispersing medium water, mixtures of water with water miscible liquids, non-aqueous media, or organic solvents or lipophilic liquids.

19. The method according to claim 1, wherein the medium to high mixing force acting on the suspension for comminution of the particles is applied by way of a high pressure process, wherein homogenizers of the piston-gap homogenizer type, the jet stream type or the French press type are used.

20. The method according to claim 1, wherein when using high pressure homogenizers the homogenization pressure is above 100 bar.

21. The method according to claim 20, wherein in that when applying high pressure homogenizers for obtaining an average PCS particle size below 1 μm the number of homogenization cycles is below 10.

22. The method according to claim 1, wherein the particle suspension obtained after said particle comminution is used either directly or after separation of the particles, in pharmaceutical and cosmetic applications.

23. The method according to claim 1, wherein the obtained suspension is further processed to intermediate products or final products.

24. The method according to claim 1, wherein the obtained suspension is further processed by way of application onto sugar pellets or by way of incorporation into matrix pellets.

25. The method according to claim 1, wherein the obtained suspension is spray dried or lyophilized.

26. The method according to claim 1, wherein the obtained suspension is used as granulating liquid, and by way of a granulation step a granulate is obtained which is applied directly or after compaction into tablets.

27. The method according to claim 1, wherein the obtained suspension is directly or after modification filled into hard or soft gelatine capsules.

28. The method according to claim 1, wherein the polydispersity index (PI) is below 0.35.

29. A method of using a particle suspension obtained from a method for the production of ultra-fine suspensions comprising: dissolving a substance which is a solid at 20° C. in a solvent to form a solution; very rapidly and substantially removing the solvent from said solution to obtain a powder comprising particles of which have an average particle size in the range of 1 to 50 μm (according to laser diffractometry); dispersing the powder in a dispersing medium to obtain a suspension; and further processing the suspension by applying medium to high forces to form a suspension comprising solid particles of which having an average particle size (according to photon correlation spectroscopy (PCS)) below 1 μm; wherein the polydispersity index of the resulting particle is decreased and wherein the substance is a medical drug, cosmetically active agent, an additive for food, a dye or a pigment, in the fields of pharmaceuticals, cosmetics, food, textiles, or agriculture.

30. The method according to claim 29, wherein the particles are separated from the dispersion medium and used in the form of tablets, capsules, creams, ointments or powders.

31. Method for the production of ultra-fine suspensions containing an active ingredient that is poorly soluble, the method comprising: dissolving the active which is a solid at 20° C. in a solvent to form a solution; spray drying the solution to remove the solvent from the solution to obtain a powder comprising particles of which have an average particle size in the range of 1 to 50 μm (according to laser diffractometry); dispersing the powder in a dispersing medium to obtain a suspension; and further processing the suspension by applying medium to high forces to form a suspension comprising solid particles of which having an average particle size (according to photon correlation spectroscopy PCS) below 1 μm; wherein the polydispersity index of the resulting particle is decreased.

* * * * *